US00PP29197P2

(12) United States Plant Patent
van Langen

(10) Patent No.: US PP29,197 P2
(45) Date of Patent: Apr. 3, 2018

(54) ***ECHEVERIA* PLANT NAMED 'AMIECH1607'**

(50) Latin Name: *Echeveria agavoides*
Varietal Denomination: AMIECH1607

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 15/530,571

(22) Filed: Jan. 30, 2017

(51) Int. Cl.
*A01H 5/02* (2018.01)

(52) U.S. Cl.
USPC ..... Plt./373
CPC ..... *A01H 5/02* (2013.01)

(58) Field of Classification Search
USPC ..... Plt./373, 372
CPC ..... A01H 5/02
See application file for complete search history.

*Primary Examiner* — Kent L Bell
(74) *Attorney, Agent, or Firm* — Samuel R. McCoy, Jr.

(57) ABSTRACT

A new and distinct *Echeveria agavoides* cultivar named 'AMIECH1607' which is characterized by thick succulent foliage with an upwardly curved attitude, arranged in a compact rosette. The green foliage exhibits a short apiculate apex that is tipped with bright red. The new variety has shown to be uniform and stable in the resulting generations from asexual propagation.

4 Drawing Sheets

Latin name of the genus and species: The Latin name of the genus and species of the novel variety disclosed herein is *Echeveria agavoides*.

Variety denomination: The inventive variety of *Echeveria* disclosed herein has been given the variety denomination 'AMIECH1607'.

BACKGROUND OF THE INVENTION

Parentage: 'AMIECH1607' is a seedling selection resulting from the self-pollination of the species, *Echeveria agavoides* (an unnamed plant). The crossing was made by the inventor in the autumn of 2012 at a commercial greenhouse in Heerhugowaard, The Netherlands. Seed from said cross was harvested, then germinated, and the resulting seedlings were then grown to a mature size. In spring of 2014, one seedling was observed to exhibit unique foliage characteristics and growth habit. The seedling was isolated for further evaluation in order to confirm the distinctness and stability of the characteristics first observed. Upon confirmation of distinctness and stability, 'AMIECH1607' was selected for commercialization in the autumn of 2015.

Asexual Reproduction: Asexual reproduction of the new cultivar 'AMIECH1607', by way of rooting leaf cuttings, was first initiated in the summer of 2016 at the inventor's commercial greenhouse in Heerhugowaard, The Netherlands. Through three subsequent generations, the unique features of this cultivar have proven to be stable and true to type.

SUMMARY OF THE INVENTION

The cultivar 'AMIECH1607' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1607'. These characteristics in combination distinguish 'AMIECH1607' as a new and distinct *Echeveria agavoides* cultivar:

1. 'AMIECH1607' exhibits thick, succulent foliage with an upwardly curved attitude;
2. 'AMIECH1607' exhibits foliage tightly arranged into a compact rosette; and
3. 'AMIECH1607' exhibits broad ovate to near oblong foliage with a short apiculate apex; and
4. 'AMIECH1618' exhibits green foliage which is tipped with bright red.

BOTANICAL DESCRIPTION OF THE PLANT

Figure 1:
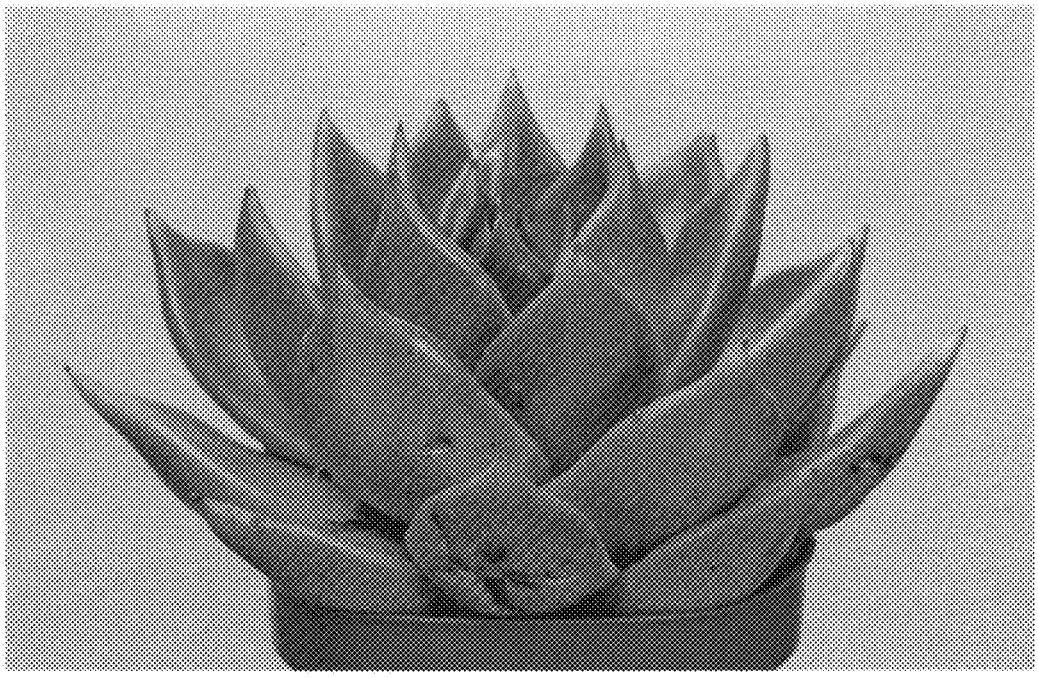
FIG. 1 illustrates, as nearly true as it is reasonably possible to make the same in color photographs of this type, an exemplary plant of 'AMIECH1607' grown in a commercial greenhouse in Heerhugowaard, the Netherlands. This plant is approximately 9 months old, shown planted in a 10 cm container.
Figure 2:
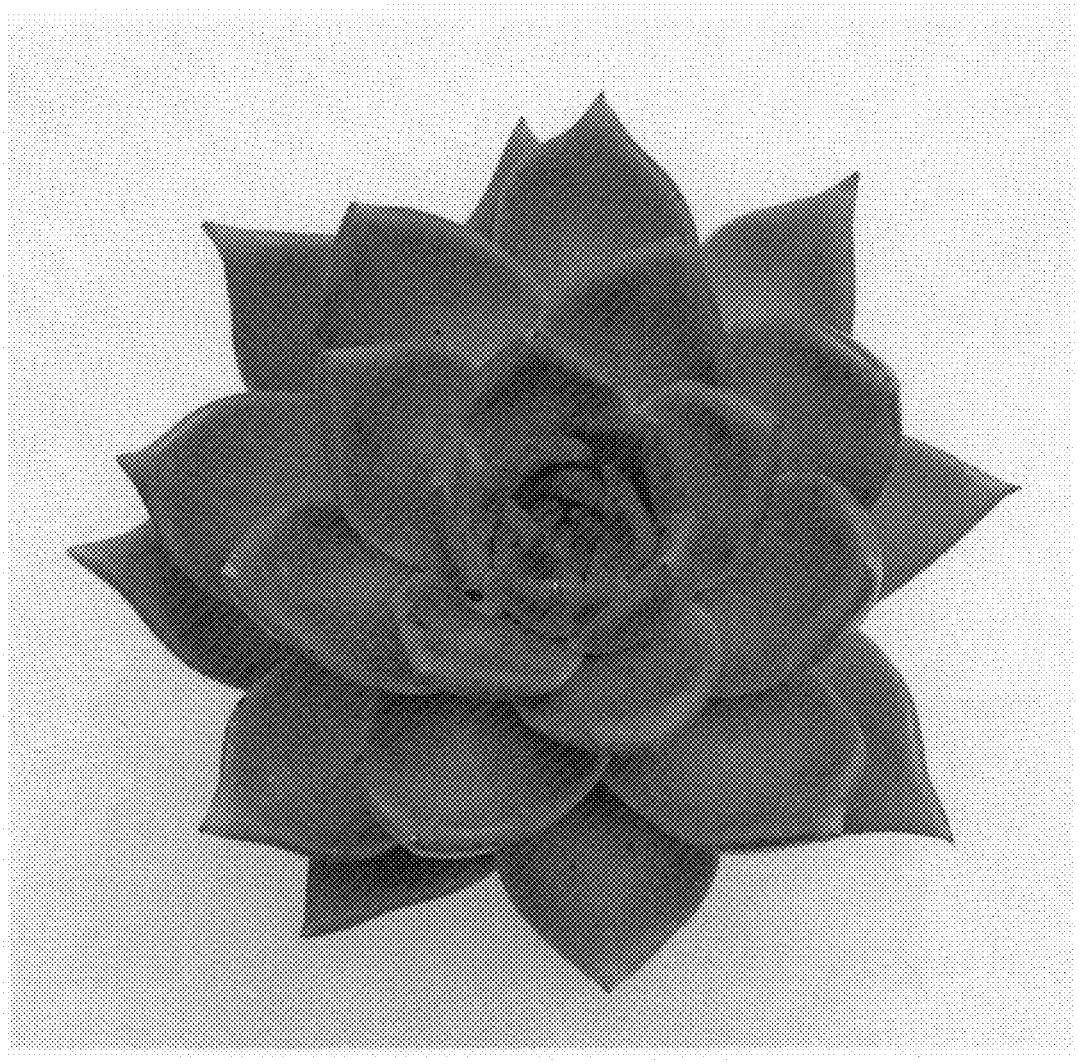
FIG. 2 illustrates, as nearly true as it is reasonably possible to make the same in color photographs of this type, the typical foliage arrangement of 'AMIECH1607'.
Figure 3:
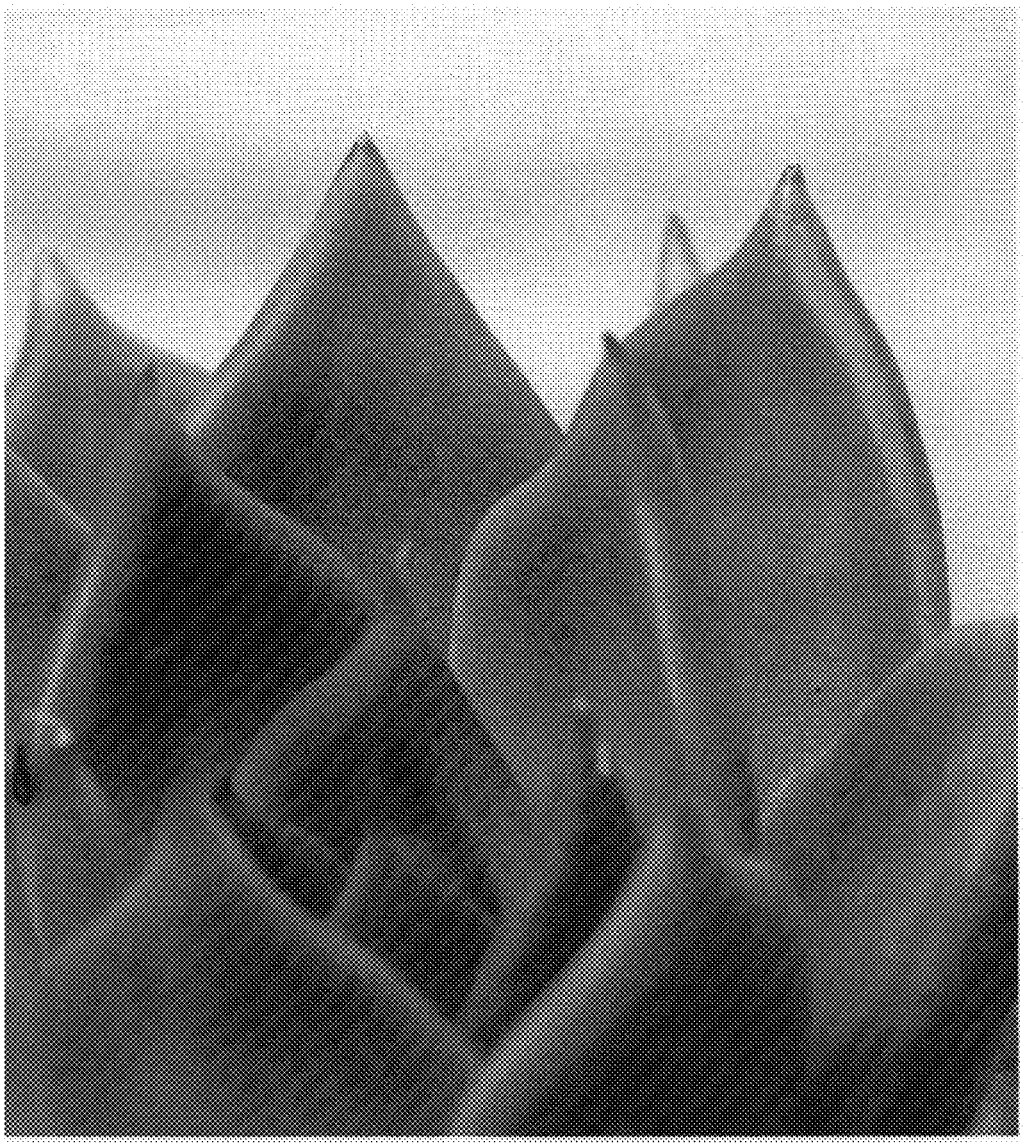
FIG. 3 illustrates, as nearly true as it is reasonably possible to make the same in color photographs of this type, the foliage color from the center of the rosette (juvenile foliage) to the outer most whorl of the rosette (mature foliage) of 'AMIECH1607'.
Figure 4:
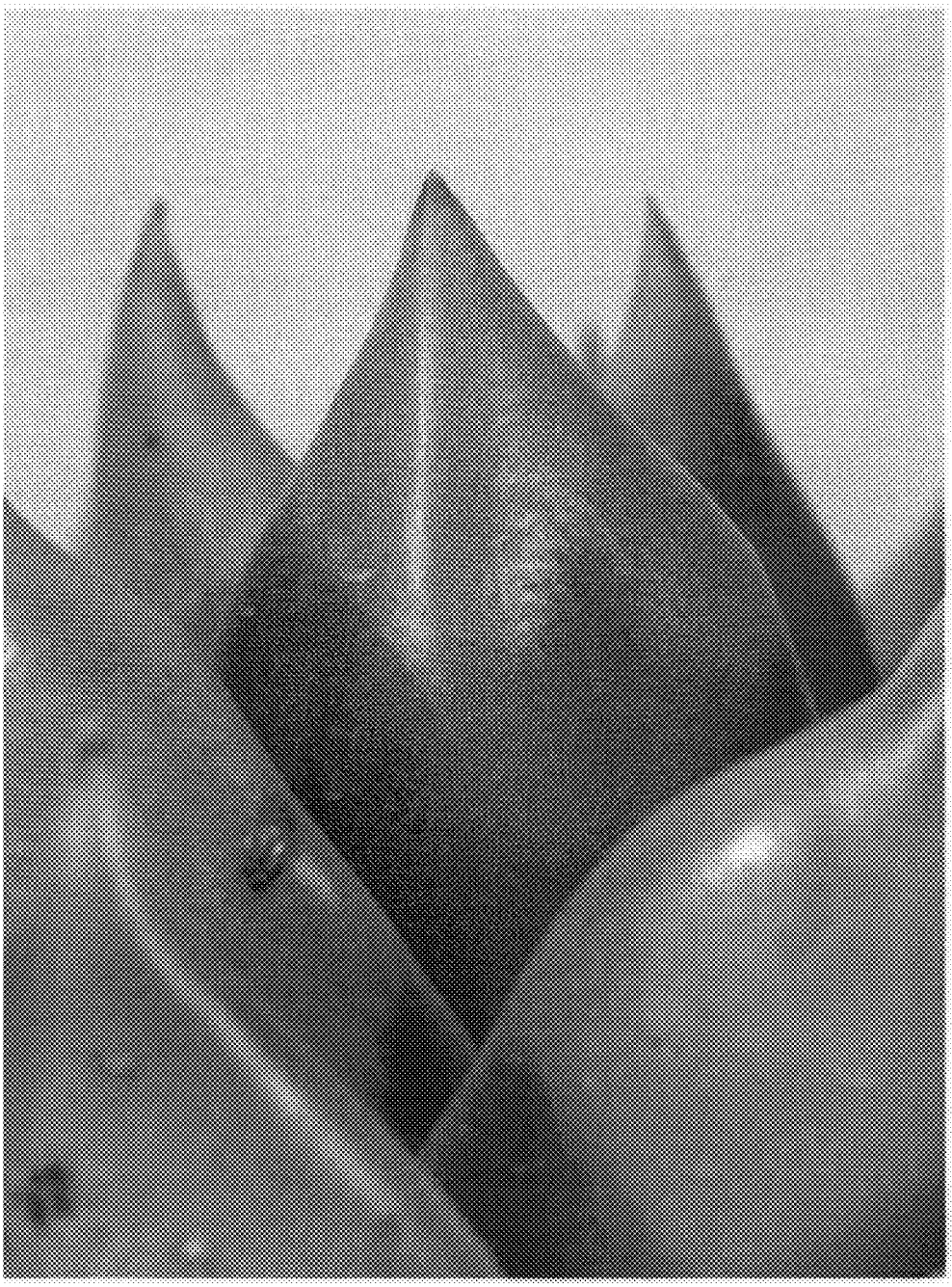
FIG. 4 illustrates, as nearly true as it is reasonably possible to make the same in color photographs of this type, the abaxial surface of the mature foliage 'AMIECH1607'.

The following observations and measurements made in November of 2016 describe averages from a sample set of six specimens of 9 months old 'AMIECH1607' plants grown in 10 cm nursery containers at commercial greenhouse in Heerhugowaard, The Netherlands. Plants were produced using conventional greenhouse production protocols for *Echeveria* which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1607' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH1607' and a comparison with the parent which is the closest known comparator an unnamed plant of, *Echeveria agavoides*, is provided below.

Plant description:

*Growth habit*.—Succulent perennial with foliage growing in a non-branched basal rosette.

*Plant shape*.—Flattened globular.

*Height from soil level to top of foliar plane*.—9.0 cm.

*Plant spread*.—Average of 17.0 cm.

*Growth rate*.—Low to moderate.

*Plant vigor*.—Low to moderate.

*Propagation*.—Type — Leaf cuttings. Time to initiate rooting — Approximately 21 to 35 days at 18 degrees Celsius. Crop time — Approximately 18 to 22 weeks to produce a marketable plant in an 11 cm container.

*Disease and pest resistance or susceptibility*.—Neither resistance nor susceptibility to typical *Echeveria agavoides* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 32 leaves per rosette.

*Shape*.—Thick, succulent leaves which are obovate to near oblong.

*Dimensions*.—7.7 cm long, 4.1 cm wide, and 1.65 cm thick, on average.

*Aspect*.—Slightly to moderately concave.

*Attitude*.—Slightly curved upward.

*Apex*.—Short apiculate.

*Base*.—Broad cuneate.

*Margin*.—Entire; not undulated or lobed.

*Pubescence, texture and luster of the adaxial surface*.—Glabrous, smooth, and moderately glossy.

*Pubescence, texture and luster of the abaxial surface*.—Glabrous, smooth, and moderately glossy.

*Color*.—Juvenile foliage, adaxial surface — General coloration is green, nearest to RHS 138B; color towards the base is a combination of yellow-green, RHS 145D, and green-white, RHS 157A; darker towards the apex, nearest to RHS 138A; apex is greyed-red, in between RHS 180C and 180D. Juvenile foliage, abaxial surface — General coloration is green, nearest to RHS 138C; fading to yellow-green, RHS 145D, towards the base; darker towards the apex, in between RHS 138A and N138B; apex is greyed-red, nearest to RHS 180D. Mature foliage, adaxial surface — General coloration is yellow-green, nearest to RHS 147C; fading lighter towards the base, a combination of RHS 148B and 148C; apex is greyed-red, nearest to RHS 180D. Mature foliage, abaxial surface — General coloration is yellow-green, in between RHS 146D and 147C, and darker towards the apex, nearest to RHS 146B; apex is greyed-red, nearest to RHS 180D.

*Venation*.—No venation is visible.

*Petiole*.—No petiole; leaves are sessile.

Inflorescence: No flowering has been observed to date.

COMPARISONS WITH THE PARENT PLANT AND CLOSEST KNOWN COMPARATOR

Plants of the new cultivar 'AMIECH1607' differ from the parent an unnamed plant of, *Echeveria agavoides*, which is also the closest known comparator, in the following characteristics described in Table 1 below.

TABLE 1

| Characteristic | 'AMIECH1607' | *Echeveria agavoides* (unnamed plant) |
|---|---|---|
| Leaf apex. | Short apiculate. | Acute. |
| Leaf thickness. | Thicker than the parent. | Thinner than 'AMIECH1607'. |
| General coloration of mature foliage. | Green to yellow-green; leaf tip is greyed-red. | Yellow-green and suffused with greyed-purple towards the apex and margins. |
| Foliage pruinose. | Not pruinose. | Moderately pruinose. |

That which is claimed is:

1. A new and distinct variety of *Echeveria agavoides* plant named 'AMIECH1607', substantially as described and illustrated herein.

* * * * *